(12) United States Patent
Weems et al.

(10) Patent No.: US 12,171,536 B2
(45) Date of Patent: Dec. 24, 2024

(54) SWIVEL HOSE COUPLING WITH OUTER GRIP

(71) Applicant: Weems Industries, Inc., Marion, IA (US)

(72) Inventors: Robert M. Weems, Marion, IA (US); Allen L. Hudson, Martelle, IA (US); Kent J. Cromer, Marion, IA (US); Marco Laubach, Marion, IA (US)

(73) Assignee: Weems Industries, Inc., Marion, IA (US)

( * ) Notice: Subject to any disclaimer, the term of this patent is extended or adjusted under 35 U.S.C. 154(b) by 0 days.

(21) Appl. No.: 18/230,244

(22) Filed: Aug. 4, 2023

(65) Prior Publication Data
US 2023/0380707 A1 Nov. 30, 2023

Related U.S. Application Data

(62) Division of application No. 14/614,486, filed on Feb. 5, 2015.
(Continued)

(51) Int. Cl.
*F16L 27/08* (2006.01)
*A61B 3/12* (2006.01)
(Continued)

(52) U.S. Cl.
CPC .......... *A61B 5/0261* (2013.01); *A61B 3/1233* (2013.01); *A61B 3/1241* (2013.01);
(Continued)

(58) Field of Classification Search
CPC ......... F16L 35/00; F16L 35/005; F16L 37/23; F16L 37/22; F16L 37/0816; F16L 37/0828; F16L 37/0824; F16L 33/30
(Continued)

(56) References Cited

U.S. PATENT DOCUMENTS 1,971,500 A * 8/1934 Palmer .................... F16L 35/00
285/119
5,316,348 A * 5/1994 Franklin ................ F16L 35/00
285/39
(Continued)

OTHER PUBLICATIONS

Innovation, Science and Economic Development Canada, Application No. 2,881,060, Office Action dated Jun. 10, 2022.
(Continued)

*Primary Examiner* — Aaron M Dunwoody
(74) *Attorney, Agent, or Firm* — Brick Gentry PC; Brian J. Laurenzo; Charles Forney (57) ABSTRACT

A water hose coupling having a swivel grip is provided. A first coupling portion with a male threaded end integral with a first larger diameter base is connected to a second coupling portion through a freely rotating connection. The second coupling portion includes a second larger diameter base. The second coupling portion further includes a coupling protrusion integral with the second larger diameter base. The coupling protrusion may have one or more barbs to interface with a hose or a threaded female coupling to interface with a male threaded connector. The coupling is connected to an end of a hose to which accessories may be attached. An outer sleeve is connected to the first larger diameter base of the first coupling portion and can freely rotate with the first coupling portion around the remainder of the apparatus and hose. The outer sleeve acts as an ergonomic grip for users to hold and rotate when using the hose and installing accessories.

3 Claims, 10 Drawing Sheets

Related U.S. Application Data (60) Provisional application No. 61/936,806, filed on Feb. 6, 2014.

(51) Int. Cl.
| | |
|---|---|
| *A61B 5/02* | (2006.01) |
| *A61B 5/026* | (2006.01) |
| *F16L 33/22* | (2006.01) |
| *F16L 33/30* | (2006.01) |
| *F16L 37/14* | (2006.01) |
| *A61B 5/00* | (2006.01) |
| *A61B 5/024* | (2006.01) |
| *A61B 5/0245* | (2006.01) |
| *A61B 5/1455* | (2006.01) |

(52) U.S. Cl.
CPC ...... *A61B 5/02007* (2013.01); *F16L 27/0816* (2013.01); *F16L 27/0824* (2013.01); *F16L 33/225* (2013.01); *F16L 33/30* (2013.01); *F16L 37/14* (2013.01); *A61B 5/02416* (2013.01); *A61B 5/02438* (2013.01); *A61B 5/0245* (2013.01); *A61B 5/14555* (2013.01); *A61B 5/14556* (2013.01); *A61B 5/6821* (2013.01); *A61B 5/6823* (2013.01); *A61B 5/6824* (2013.01); *A61B 2560/0431* (2013.01)

(58) Field of Classification Search
USPC ............. 285/114, 115, 116, 276, 259, 121.5, 285/121.6
See application file for complete search history.

(56) References Cited

U.S. PATENT DOCUMENTS

| | | |
|---|---|---|
| 5,367,925 A | 11/1994 | Gasparre |
| D356,858 S | 3/1995 | Folkman |
| 5,572,912 A | 11/1996 | Gasparre |
| 5,816,622 A * | 10/1998 | Carter ............... F16L 35/00 138/110 |
| 2002/0070550 A1 | 6/2002 | Lin et al. |
| 2004/0140376 A1* | 7/2004 | Alexander ........... F16L 35/005 239/152 |
| 2006/0208110 A1 | 9/2006 | Guo |
| 2006/0208483 A1* | 9/2006 | Guo ................ F16L 35/005 285/275 |
| 2015/0219259 A1 | 8/2015 | Weems et al. |

OTHER PUBLICATIONS

Innovation, Science and Economic Development Canada, Application No. 2,881,060, Office Action dated Oct. 27, 2021.
Innovation, Science and Economic Development Canada, Application No. 2,881,060, Office Action dated Mar. 26, 2021.

* cited by examiner

SWIVEL HOSE COUPLING WITH OUTER GRIP

CROSS-REFERENCE TO RELATED APPLICATION

This application is a divisional application of U.S. Nonprovisional patent application Ser. No. 14/614,486 filed Feb. 5, 2015 and entitled Swivel Hose Coupling with Outer Grip. U.S. Nonprovisional patent application Ser. No. 14/614,486 claims priority from U.S. Provisional Application Ser. No. 61/936,806 filed Feb. 6, 2014 and entitled WATER HOSE COUPLING WITH SWIVEL GRIP. The contents of U.S. Nonprovisional patent application Ser. No. 14/614,486 and U.S. Provisional Application Ser. No. 61/936,806 are hereby incorporated in their entireties by reference.

FIELD OF THE INVENTION

The present invention generally relates to couplings for hoses. More specifically, the present invention relates to couplings on one end of a hose having a freely rotating end that rotates independently of the remainder of the coupling attached to the end of the hose. Additionally, the coupling may include a sleeve grip attached to the coupling and extending over and surrounding a portion of a hose.

BACKGROUND

Traditional water hoses used in gardens, as well as for industrial purposes, are composed of resilient materials, such as plastic or rubber, with reinforcements, such as metal wire, interwoven into the materials. Additionally, each end of the water hose includes a coupling. Typically one end is a female coupling and the other end is a male coupling. These couplings are traditionally made of metal, such as brass. Users of water hoses typically use more than one accessory with their water hose and, thus, must repeatedly install and remove the accessories from the water hose. Accessories for traditional water hoses can include nozzles, spray guns, sprinklers, pressure washers, extensions, wands, and various other devices.

Typically, the female end includes recessed threads to accept and couple with a complementary male threaded water source. The male end of a hose also include threads on its outer projecting surface to accept and couple with a complimentary female threaded accessory or other hose coupling. The female coupling can sometimes include a freely rotating installation swivel coupling that allows it to be more easily coupled with the male water source coupling. However, the freely rotating female coupling only rotates until it is tightened on the water source's male coupling end.

The installation and removal of multiple accessories can become time consuming and frustrating as fitting an accessory to the male coupling of a water hose by rotating the water hose onto the accessory can be difficult, especially when the hose and coupling are already wet and heavy (especially if filled with water). Furthermore, the action of aligning and rotating the water hose onto the accessory can be additionally difficult when water is still flowing from the hose and leaking from the male end as the accessory is installed or removed. This is especially true for the elderly, children, and people suffering from arthritis. Additionally, rotating the coupling and accessory to properly mount or unmount the accessory to and from the hose can be cumbersome and tiring as the coupling is attached to the remainder of the water hose that resists rotational force applied to it.

Similarly, the installation and removal of a water hose from a water source can be frustrating and cumbersome. Even if the water hose's female coupling rotates independently of the hose during installation it is typically still difficult to align and rotate the small coupling portions together. This can be made additionally difficult if the hose coupling and/or water source coupling is wet or water is flowing from one of the couplings. Again, this is especially true for the elderly, children, and people suffering from arthritis.

Moreover, using a water hose that has been coiled for storage by pulling on the hose or an accessory attached to the hose, often-times puts strain on the user holding the accessory as the hose requires to be uncoiled as it is pulled. This action causes the hose to thrash and often kink if the user does not stop pulling and rotate the hose and accessory to allow the hose to uncoil properly. This is again time consuming and frustrating. Again, this especially affects the elderly, children, and the arthritic. Accordingly, there is a need for a device that allows for easier coiling and uncoiling of a stored water hose and accessory as well as allows for easier mounting and removal of an accessory from a water hose.

Water hose grips are known in the art as shown in U.S. Pat. No. 5,333,650 to Folkman. Grips provide a more ergonomic shape for users to hold as they utilize their water hose. Additionally, grips may add rigidity and strength to an end of a hose. Moreover, grips and swivels known in the art allow for an installation swivel. An installation swivel is one that freely rotates during the installation of a coupling to an accessory or water source, but becomes rigid and non-moving once fully tightened on the aforementioned accessory or water source coupling. Therefore, there is a need for a coupling/grip that rotates, even after installation of an accessory, with the male coupling end relative to a water hose to aid in installing and removing accessories from a male end of the water hose and aid in the use of an attached accessory. Specifically, the aforementioned live swivel coupling/grip allows for the rotation of an installed accessory during use that will rotate independently of the attached hose. Since the hose on a non-swivel installation resists rotation by a user, additional torqueing stress is placed on the user, specifically their wrist, to use the hose and attached accessory without a swivel coupling/grip. Therefore, there is a need for a live swivel coupling/grip that reduces and/or eliminates the need for additional torque from the user to compensate for the hose resisting rotation.

Additionally, couplers for air hoses currently known are typically made of metal such as steel or brass and are of a cylindrical form connector connected to a source of air. The cylindrical connector is able to receive male connectors from different tools to be connected to the air source. The male connector comes in different variations but typically allow a tapered nose to interface and seal around the cylindrical connector. Additionally, the tapered nose typically includes one or more radial protrusions around the circumference of the nose to seal the connection between the male connector and the female cylindrical connector. Thus, when the male connector is inserted in the cylindrical body, there are complementary, engaging portions of the cylindrical connector to hold the male connector in its connected position. The arrangement is such that the male connector can be manually inserted or removed in a fairly quick manner without having to thread parts together.

Swivel couplings used with air hoses are known in the art as shown in U.S. Pat. No. 3,873,062 to Adams, et al. Typical, as discussed above, air hose swivel connectors utilize a tapered projection on the accessory to be connected that it received by a coupling portion having a complementary design on the air hose. The tapered projection is able to rotate along its longitudinal axis because of the locking mechanism within the receiving coupling portion on the air hose. Alternatively, air hoses use a single ball bearing end that moves within one end of a coupling portion of the air hose and connects to another push fitting coupling portion on the other end. The push fitting accepts a complementary push fitting on an air hose accessory to be mounted on the air hose.

The above is not conducive to water applications as it is more likely to restrict water flow as the single ball bearing allowing movement constricts the opening available for water/air to flow through. This is not an issue in compressed air hoses as the restriction can improve the pressure of the air coming from the end of the hose. But on water applications it can unnecessarily boost the pressure and reduce volume coming from the end of the hose which is unwanted in most water applications.

SUMMARY

The present invention provides a novel coupling and sleeve device which reduces and/or eliminates the above-identified draw-backs. The device of the present invention includes a freely rotating coupling on the end of a hose. Furthermore, the preferred embodiment of the coupling of the present invention is connected to a rigid sleeve that protrudes backwards from the coupling and surrounds a portion of the hose. In the preferred embodiment, the rigid outer sleeve can freely rotate with the coupling around the end of the hose it surrounds. In some embodiments the sleeve also acts as a grip to improve the user's ability to hold the hose, especially while inserting or removing an accessory from the coupling.

The coupling of the present invention includes a first portion and a second portion. In the preferred embodiment, the first portion comprises a circular male threaded end for attachment to accessories or other hoses, wherein the male threaded end is connected to a larger diameter first base. The preferred embodiment also includes a second portion comprising a second base that which is connected to and integral with a coupling projection that is a barbed tube. The barbed tube allows for the coupling to connect to and remain within the end of a hose. The first and second portions of the coupling are connected by a freely rotating connection that allows each portion of the coupling to freely rotate with respect to each other about a longitudinal axis therethrough.

In the preferred embodiment, the freely rotating connection is established by a track integrated with either the first or second coupling portion. The track accepts one or more ball bearings inserted through an access port of the first coupling portion. The access port is subsequently sealed using a pin, screw, or other means to seal the access port. It is also contemplated that one or more friction-reducing/slick washers could be substituted or used in conjunction with the ball bearings in the track to create the freely rotating connection. In an alternative embodiment of the present invention, it is contemplated that a third coupling portion connects the first and second coupling portions and allows the first coupling portion to rotate independently of the second coupling portion.

In the preferred embodiment of the present invention, an outer sleeve connects with the coupling and extends backwards from the coupling to completely surround a portion of the hose. In at least one embodiment, this sleeve acts as a grip for the end of the hose. Furthermore, in at least one embodiment, the sleeve gives additional rigidity and strength to the portion of the tube overlapped by the sleeve. An additional benefit to this configuration is that the sleeve provides additional protection to the coupling projection from outside forces such as bending the hose or stepping on the hose. Furthermore, the sleeve also provides additional protection to the inner surface of the hose from forces applied to it by the coupling projection due to outside forces applied to the end of the hose such as bending the hose.

The preferred embodiment of the present invention allows for the reduction of forces felt by a user due to the freely rotating coupling as a hose is coiled or uncoiled, as well as during general use, and also provides an improved grip for easier mounting and unmounting of hose accessories to and from a hose. The added diameter of the sleeve and ergonomic shape also provides an easier area to grip for people with decreased hand strength such as children, the elderly, the injured and/or disabled, as well as people suffering from arthritis. In fact, both of the above-identified benefits are especially helpful for senior citizens, children, and/or people with arthritis or other disabilities and/or injuries.

DETAILED DESCRIPTION

The following is a detailed description of an apparatus 100 for a hose coupling (sometimes "apparatus"). One particular use of such apparatus 100 is at one or more ends of a water hose. For ease of discussion and understanding, the following detailed description may refer to the apparatus as a male swivel, male swivel end for a water hose, male hose coupling, water hose coupling, water hose coupling with attached coupling sleeve, and/or a hose coupling with attached coupling sleeve. However, it will be appreciated by one skilled in the art that an apparatus 100 of the present invention may be used in any number of circumstances, including, but not limited to, hoses used to transport liquids other than water, hose accessories, and/or other hose types.

Figure 1:
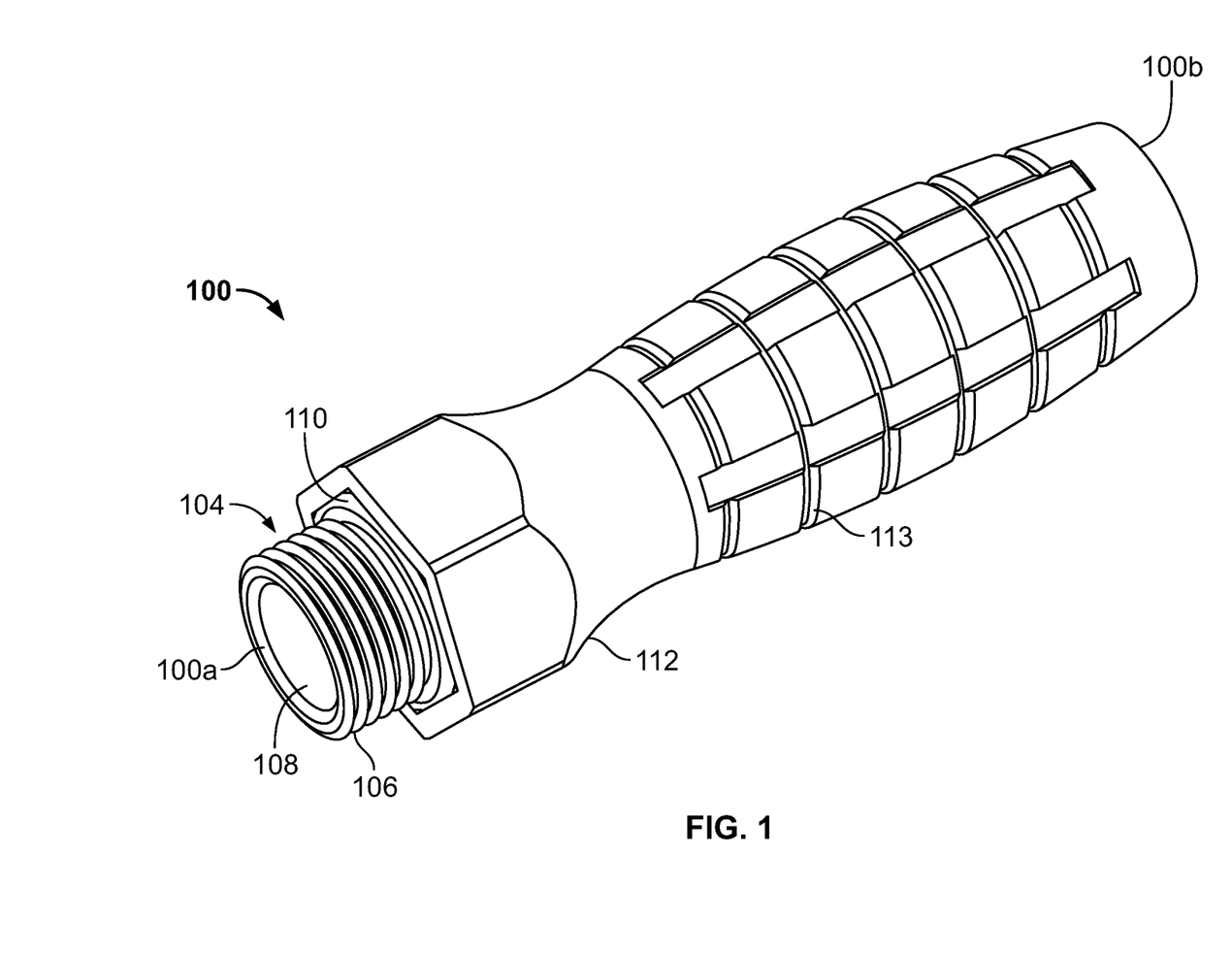
FIG. 1 is a perspective view of an embodiment of a freely rotating hose coupling device with an outer sleeve of the present invention.

Referring to FIG. 1, an apparatus 100 of the present invention is shown. The apparatus 100 includes a first end 100*a* and a second end 100*b*. The first end 100*a* comprises an adapter male assembly also referred to as a first coupling portion 104. The first coupling portion 104 has a cylindrical outer surface of threads 106. The cylindrical outer surface of threads 106 has a first inner opening 108 allowing for material contained within an attached hose 102 (shown in FIG. 4) to flow freely. The cylindrical outer surface of threads 106 is connected to a first larger diameter base 110. The first larger diameter base 110 and the cylindrical outer surface of threads 106 constitute the traditional male end of a water hose. The first larger diameter base 110 includes a second inner opening 109 (shown in FIG. 4) to accept the male stem of a second coupling portion 114 (shown in FIG. 2) as described below. In the preferred embodiment, the first coupling portion 104 is made of metal. However it should be understood by one skilled in the art that any rigid material able to withstand the stresses associated with the chosen application for the hose 102 will suffice. As shown in FIG. 1, the first larger diameter base 110 is connected to an outer sleeve 112. This outer sleeve 112 protrudes back for a predetermined length to the second end 100*b*. The second end 100*b* of the present invention is designed to accept and interface with a hose 102 having a ⅝ inch diameter, however any diameter hose 102 may be used without departing from the scope of the invention.

Figure 2:
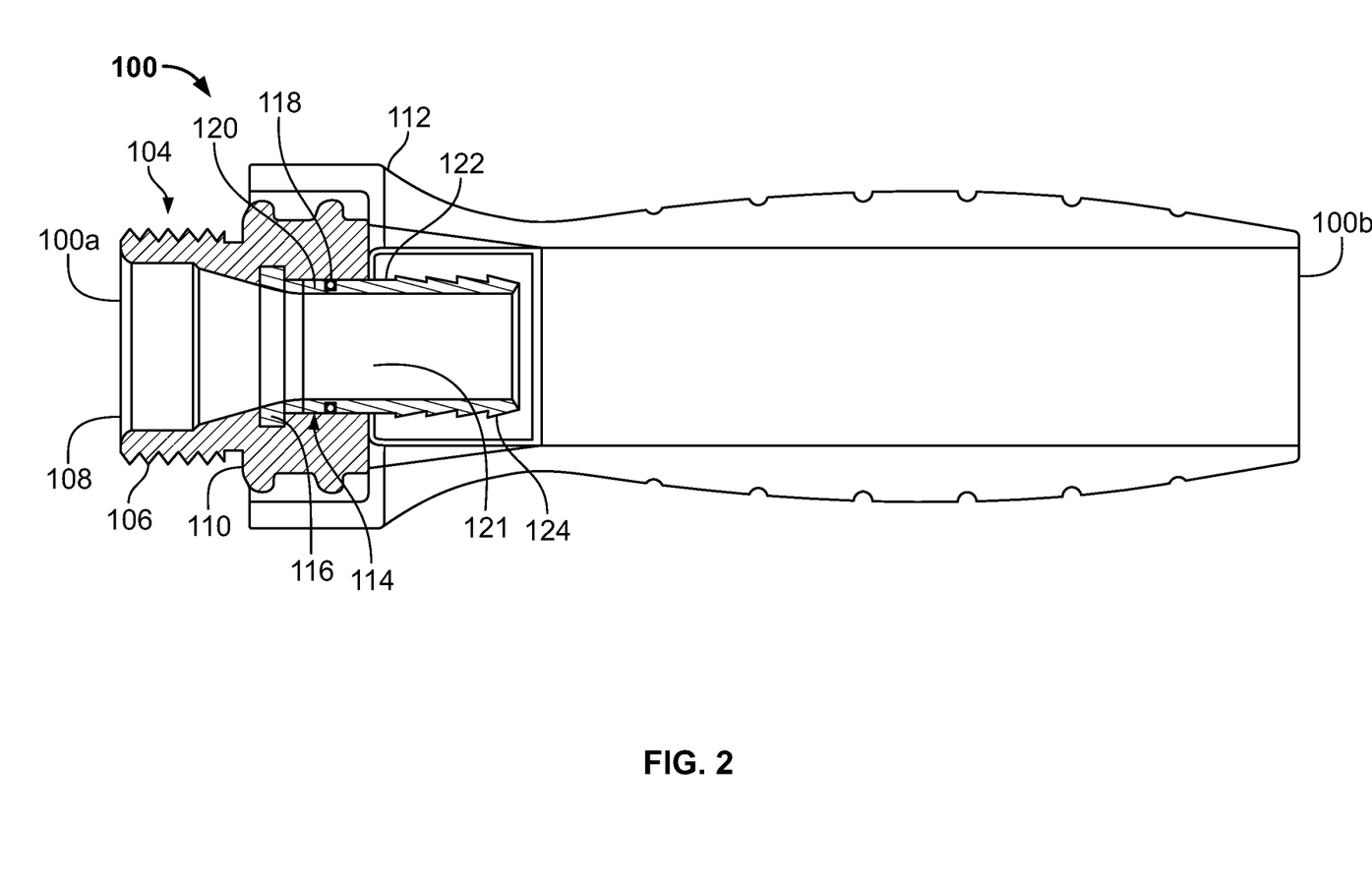
FIG. 2 is a cross-sectional side view of an embodiment of a freely rotating hose coupling device with an outer sleeve of the present invention.

Referring to FIG. 2, the apparatus 100 also includes a second coupling portion 114 attached to the first coupling portion 104 via a male stem wherein the connection creates a freely rotating connection 116. The freely rotating connection 116 along with the first and second coupling portion 104 and 114 are also known as the male straight swivel end for a water hose. In the preferred embodiment, the freely rotating connection 116 includes an O-ring 118; however, it should be appreciated by one skilled in the art that the O-ring 118 may be excluded, moved, and/or additional O-rings 118 may be placed throughout the invention without departing from the scope of the invention. The freely rotating connection 116 allows the first coupling portion 104 to rotate along a longitudinal axis around the second coupling portion 114 which constitutes a straight swivel.

The second coupling portion 114 has a first end 114*a* and a second end 114*b*. The first end 114*a* of the second coupling portion 114 includes the male stem which is integral with a second larger diameter base 120. The second larger diameter base 120 includes a third inner opening 121 allowing for material contained within an attached hose 102 (shown in FIG. 4) to flow freely through. The second larger diameter base 120 may taper as it extends toward the second end 114*b* of the second coupling portion 114. However, any shape suitable to the application may be used for the second coupling portion 114 without departing from the scope of the invention. Additionally, it is contemplated that the tapered end of the second coupling portion 114 could be substituted by a female, threaded protrusion (shown in FIG. 12) to connect to the male end of another device without departing from the scope of the present invention. This configuration would allow a standard, non-straight swivel hose to be adapted with the device of the present invention.

The second end 114*b* of the second coupling portion 114 is integral with a coupling protrusion 122. The coupling protrusion 122 has a first end 122*a* and a second end 122*b*. The preferred embodiment of the present invention shows the coupling protrusion 122 having a smaller diameter than the second coupling portion 114. However, it should be appreciated by one skilled in the art that the diameter of the coupling protrusion 122 may be modified without departing from the scope of the invention. The coupling protrusion 122 extends from the first end 122*a* for a predetermined length and concludes at the second end 122*b*. The preferred embodiment of the coupling protrusion 122 is a tubular shaped module having one or more barbs 124 on its outer surface. However, it should be appreciated by one skilled in the art that the coupling protrusion could be smooth, textured, knurled, threaded, etc. and take on various shapes without departing from the scope of the invention. The preferred embodiment of the present invention contemplates the second coupling portion 114 as well as the coupling protrusion 122 be made of metal. However, it should be appreciated by one skilled in the art that any rigid material able to withstand the stresses associated with the chosen application for the hose 102 will suffice.

Figure 4:
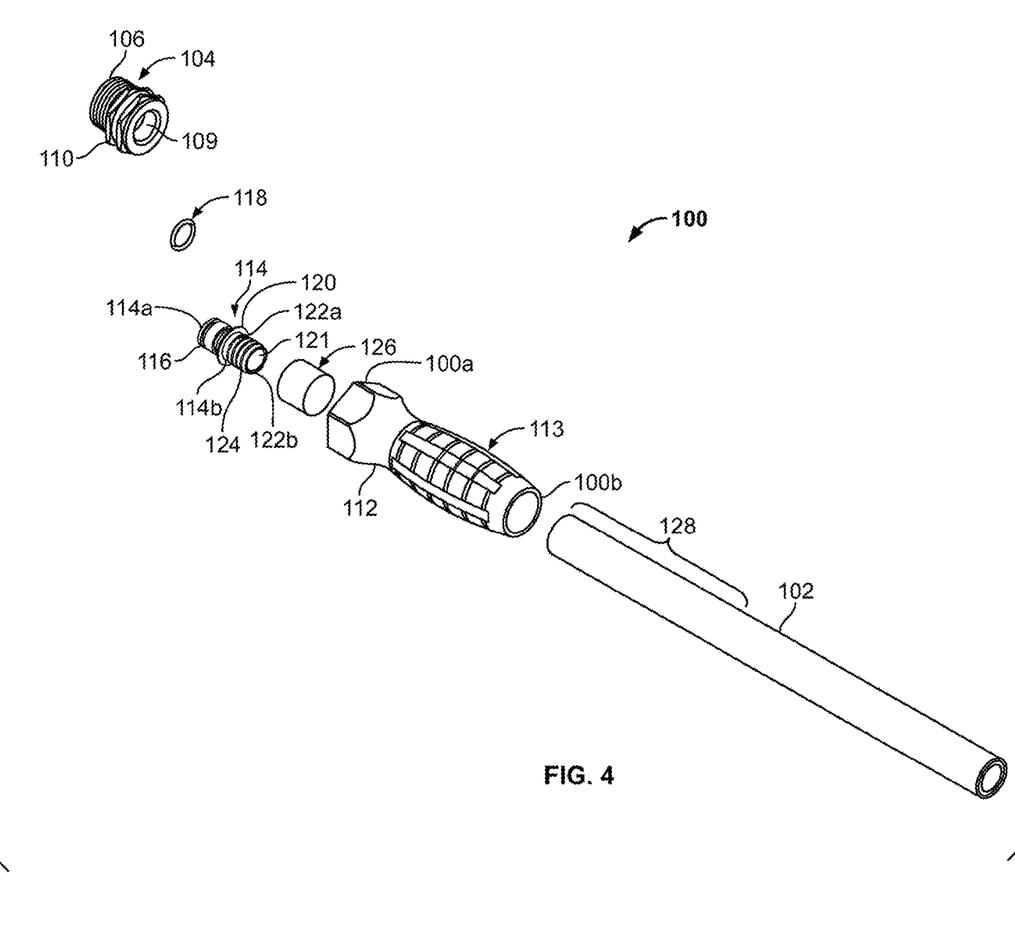
FIG. 4 is an exploded view of an embodiment of a freely rotating hose coupling device with an outer sleeve of the present invention.

The barbs 124 of the coupling protrusion 122 act as a connecting and sealing mechanism for the apparatus' 100 connection with a hose 102 (shown in FIG. 4). Each barb 124 extends into the inner surface of a hose 102 mating the hose 102 to the apparatus 100. Because the second coupling portion 114 and connected coupling protrusion 122 move upon a longitudinal axis independently of the first coupling protrusion 104 and outer sleeve 112, the hose 102 connected to the second coupling portion 114 via the coupling protrusion 122 can move independently of any hose accessory attached to, or movement of, the first coupling portion 104 via the cylindrical outer surface of threads 106.

Figure 3:
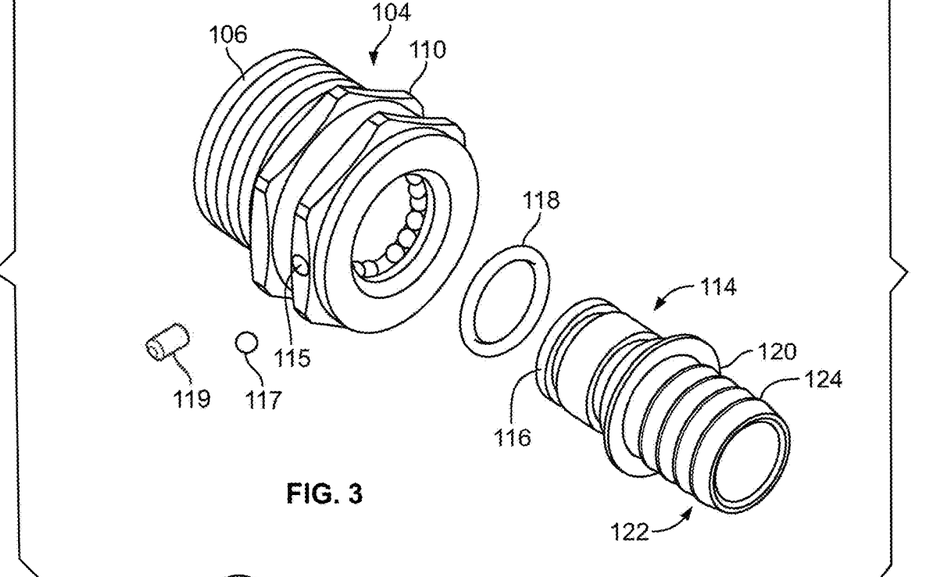
FIG. 3 is an exploded view of the preferred embodiment of a freely rotating hose coupling device of the present invention.

As shown in FIG. 3 an exploded view of the preferred embodiment of the present invention is shown. A freely rotating connection 116 is formed by the interfacing of the first coupling portion 104 with the second coupling portion 114. Also shown in the embodiment, is an O-ring 118 included in the freely rotating connection 116 to aid in sealing the first and second coupling portions 104 and 114 to one another. Again, the second coupling portion 114 is shown comprising of a coupling protrusion 122 having one or more barbs 124 integral with the second larger diameter base 120.

Additionally, FIG. 3 illustrates the preferred embodiment and the integration of an interior track in the first coupling portion 104. The interior track can accept one or more ball bearings, friction-reducing/slick washers, and/or similar friction reducing components 117 to aid in the ease of the rotation of the freely rotating connection 116. In the preferred embodiment, the interior track is entirely encapsulated by the male stem of the second coupling portion 114 and the first larger diameter base 110 of the first coupling portion 104. The track is accessed by an access port/opening 115 in the first larger diameter base 110. The access port 115 of the preferred embodiment of the present invention allows for the insertion of one or more ball bearings 117 once the first and second coupling portions 104 and 114 have been connected. In the preferred embodiment, the access port 115 is sealed by a corresponding locking/covering pins 119. However, it should be appreciated by one skilled in the art that multiple access ports 115 and/or locking pins 119 or other covering mechanisms can be utilized without departing from the scope of the invention. It should also be appreciated by one skilled in the art that any friction reducing component may be adapted and used within the hose coupling 100 without departing from the scope of the present invention.

Figure 3A:
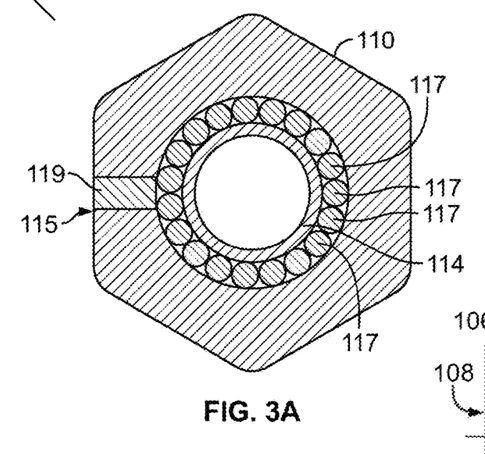
FIG. 3a is a cross-sectional view of the preferred embodiment of the first coupling portion with interior track and access port with pin of a freely rotating hose coupling device of the present invention.

Referring now to FIG. 3a, a cross-sectional view of the first coupling portion 104 of the preferred embodiment is shown. Again, the interior track for accepting one or more ball bearings 117 is shown within the first larger diameter base 110 of the first coupling portion 104. It should be appreciated by one skilled in the art that the placement of the track within the apparatus 100 may be positioned in various parts of the coupling portions 104 and 114 without departing from the scope of the invention. Additionally illustrated in FIG. 3a is the access port 115 on the left side of the first larger diameter base 110 of the first coupling portion 104. Inserted and sealing the access port 115 is a pin 119 so that the ball bearings are not able to escape the interior track once placed within said interior track. As depicted in FIG. 3a, the ball bearings 117 within the track cannot escape the track via the first or second interior opening 108 and 109 as the male stem of the second coupling portion 114 encapsulates that track and the ball bearings 117 within.

Figure 3B:
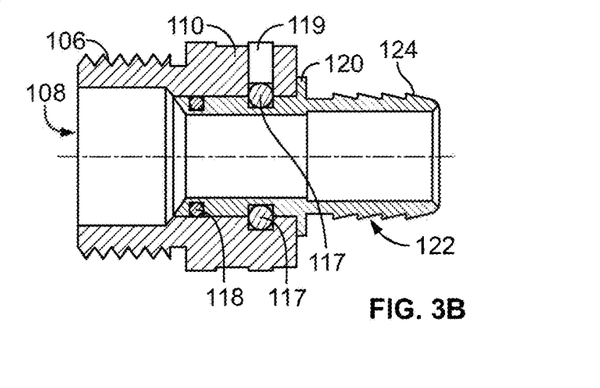
FIG. 3b is a cross-sectional view of the preferred embodiment of a freely rotating hose coupling device of the present invention.

Looking now to FIG. 3b, the preferred embodiment of the apparatus 100 is shown in a cross-sectional side view. The first coupling portion 104 is again shown connected with the male stem of the second coupling portion 114 creating a freely rotating connection 116. The freely rotating connection of the preferred embodiment is enhanced by utilizing a track between the first and second coupling portions 104 and 114 that holds one or more ball bearings, friction-reducing/slick washers, or similar friction reducing components 117. The friction reducing component(s) 117 can be inserted into the apparatus 100 via an access port 115 depicted at the top of the figure. The access port 115 is then sealed by a pin 119 of complimentary design so that the friction reducing components 117 cannot escape the track. This enhanced freely rotating connection 116 along with the first and second coupling portion 104 and 114 are also known as the male straight swivel end for a water hose. In the preferred embodiment, the freely rotating connection 116 includes an O-ring 118; however, it should be appreciated by one skilled in the art that the O-ring 118 may be excluded, moved, and/or multiple O-rings 118 may be utilized without departing from the scope of the invention. The freely rotating connection 116 allows the first coupling portion 104 to rotate along a longitudinal axis around the second coupling portion 114 which constitutes a straight swivel.

Here again, in the preferred embodiment, the second coupling portion 114 has a first end 114a and a second end 114b. The first end 114a of the second coupling portion 114 includes the male stem which is integral with a second larger diameter base 120. The second larger diameter base 120 includes a third inner opening 121 allowing for material contained within an attached hose 102 (shown in FIG. 4) to flow freely through to the first inner opening 108. The second larger diameter base 120 may taper as it extends toward the second end 114b of the second coupling portion 114. However, any shape suitable to the application may be used for the second coupling portion 114 without departing from the scope of the invention. Additionally, it is contemplated that the tapered end of the second coupling portion 114 could be substituted by a female, threaded protrusion (FIG. 12) to connect to the male end of another device without departing from the scope of the present invention. This configuration would allow a standard, non-straight swivel hose to be adapted with the device of the present invention.

The second end 114b of the second coupling portion 114 of the preferred embodiment forms a coupling protrusion 122. The coupling protrusion 122 has a first end 122a and a second end 122b. The first end 122a of the coupling protrusion 122 is integral with the second larger diameter base 120 of the second coupling portion 114. The preferred embodiment of the present invention shows the coupling protrusion 122 having a smaller diameter than the second coupling portion 114. However, it should be appreciated by one skilled in the art that the diameter of the coupling protrusion 122 may be modified without departing from the scope of the invention. The coupling protrusion 122 extends from the first end 122a for a predetermined length and concludes at the second end 122b. The coupling protrusion 122 is a tubular shaped module having one or more barbs 124 on its outer surface. The preferred embodiment of the present invention contemplates the second coupling portion 114 as well as the coupling protrusion 122 be made of metal. However, it should be appreciated by one skilled in the art that any rigid material able to withstand the stresses associated with the chosen application for the hose 102 will suffice.

The barbs 124 of the coupling protrusion 122 act as a connecting and sealing mechanism for the apparatus' 100 connection with a hose 102 (shown in FIG. 4). Each barb 124 extends into the inner surface of a hose 102 mating the hose 102 to the apparatus 100. Because the second coupling portion 114 and connected coupling protrusion 122 move upon a longitudinal axis independently of the first coupling protrusion 104 and outer sleeve 112, the hose 102 connected to the second coupling portion 114 via the coupling protrusion 122 can move independently of any hose accessory attached to, or movement of, the first coupling portion 104 via the cylindrical outer surface of threads 106.

Referring now to FIG. 4, an exploded view of an embodiment of the present invention is shown. Again, a freely rotating connection 116 connects the first coupling portion 104 with the second coupling portion 114. Also shown in the embodiment, is an O-ring 118 included in the freely rotating connection 116 to aid in sealing the first and second coupling portions 104 and 114 to one another. Again, the second coupling portion 114 is shown connected to a coupling protrusion 122 having one or more barbs 124. In the embodiment illustrated in FIG. 4 a ferrule 126 is shown to further enhance the connection and seal between the hose 102 and the second coupling portion 114 via the coupling protrusion 122 with one or more barbs 124. The ferrule 126 is used as would be understood by one skilled in the art and may be utilized with any of the embodiments of the invention described herein.

Figure 5:
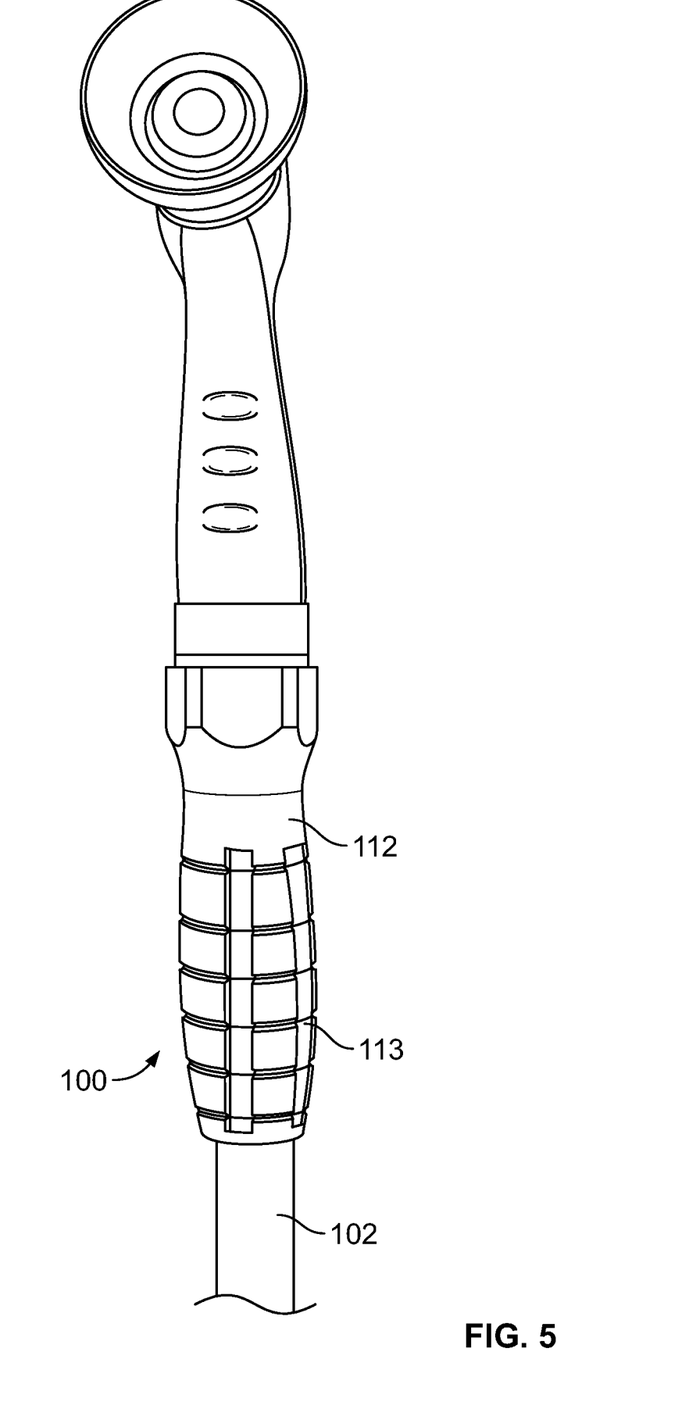
FIG. 5 is a perspective view of an embodiment of a freely rotating hose coupling device with an outer sleeve of the present invention with a hose accessory attached to the male coupling end.
Figure 6:
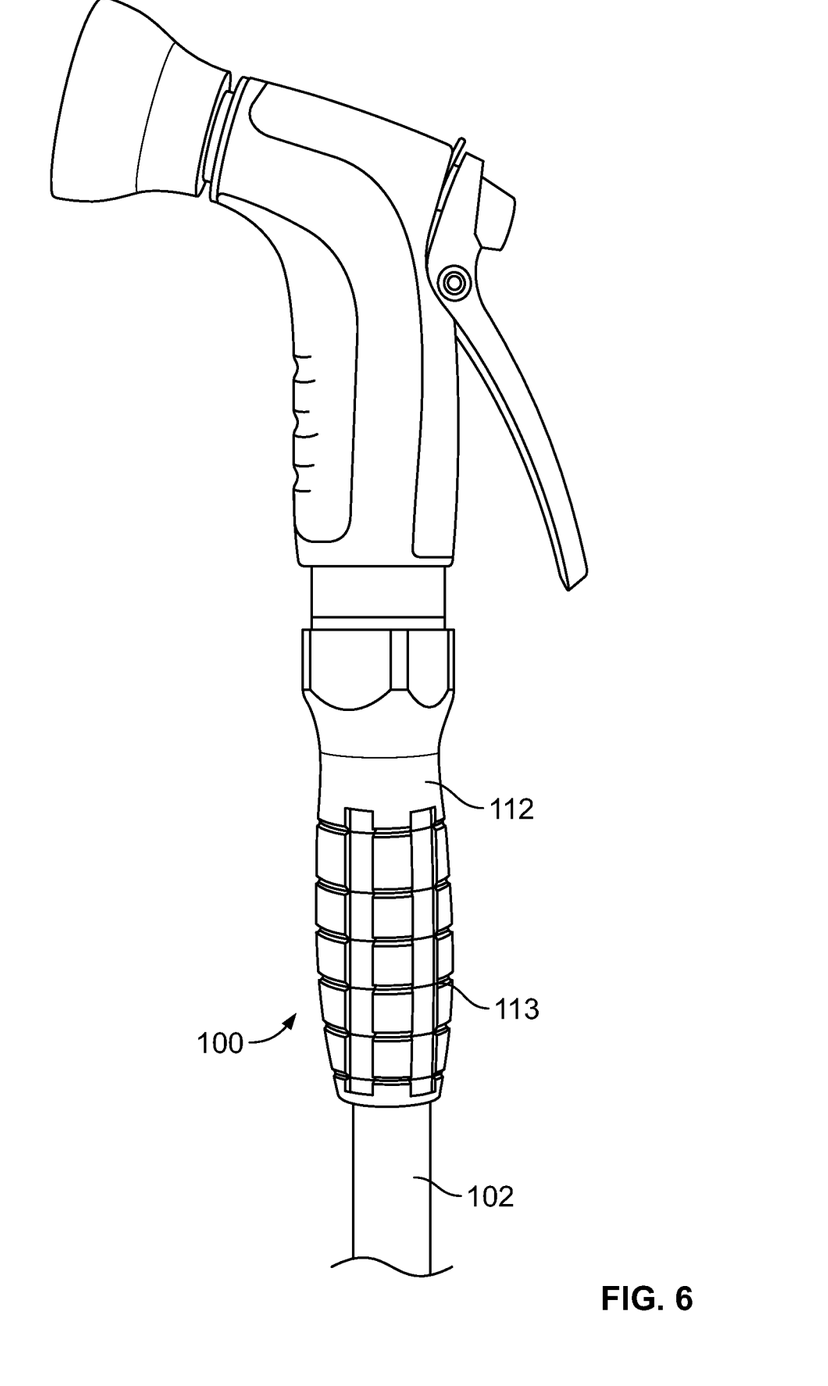
FIG. 6 is a perspective view of an embodiment of a freely rotating hose coupling device with an outer sleeve of the present invention with a hose accessory attached and rotated on the male coupling end.

It is contemplated that the outer sleeve completely surrounds a portion of the attached water hose. However, it should be appreciated by one skilled in the art that various configurations of the outer sleeve are possible that may or may not completely surround a portion of the attached water hose without departing from the scope of the invention. Additionally, FIG. 5 illustrates an accessory water hose nozzle attached to the apparatus 100. FIG. 6 illustrates the same accessory water hose nozzle rotated 90 degrees while still attached to the apparatus 100. The water hose coupling 100 may be used with any accessories traditionally used with water hoses, including, but not limited to, nozzles, spray guns, sprinklers, pressure washers, extensions, wands, and various other devices. In addition, it is contemplated that the water hose coupling 100 may be utilized to attach an additional hose in order to provide a swivel connection therebetween.

Figure 7:
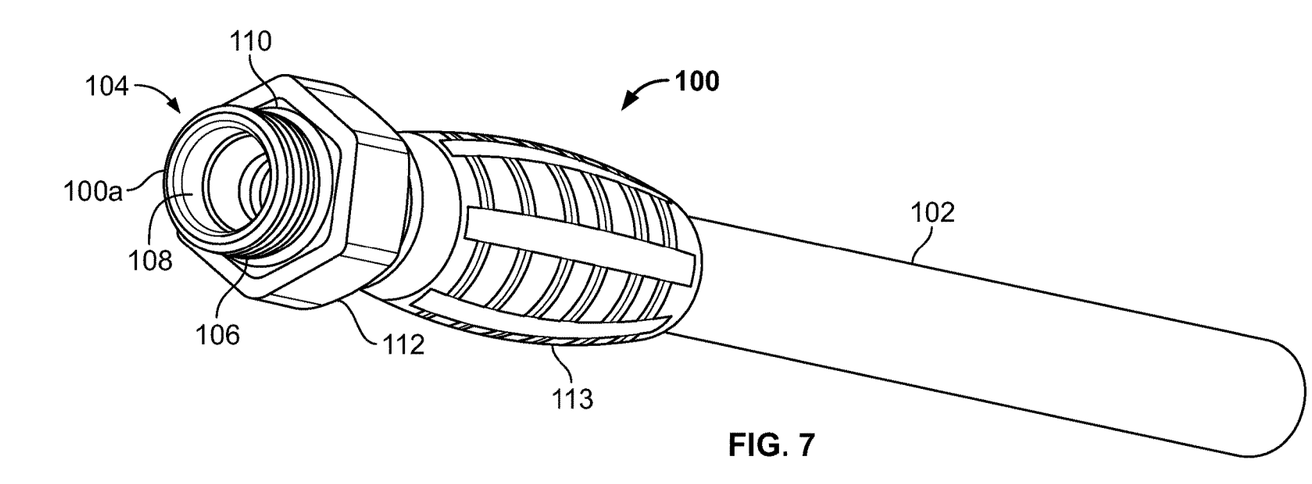
FIG. 7 is a perspective view of an embodiment of a freely rotating hose coupling device with an outer sleeve of the present invention.

Referring to FIG. 7, an apparatus 100 of the present invention with a connected hose is shown. The apparatus 100 includes a first end 100a and a second end 100b. The first end 100a comprises an adapter male assembly also referred to as a first coupling portion 104. The first coupling portion 104 has a cylindrical outer surface of threads 106. The cylindrical outer surface of threads 106 has a first inner opening 108 allowing for material contained within an attached hose 102 (shown in FIG. 4) to flow freely. The cylindrical outer surface of threads 106 is connected to a first larger diameter base 110. The first larger diameter base 110 and the cylindrical outer surface of threads 106 constitute the traditional male end of a water hose. The first larger diameter base 110 includes a second inner opening 109 (shown in FIG. 4) to accept the male stem of the second coupling portion 114. As shown in FIG. 1, the first larger diameter base 110 is connected to an outer sleeve 112. This outer sleeve 112 protrudes back for a predetermined length to the second end 100b. The second end 100b of the present invention is designed to accept and interface with a hose 102 having a ⅝ inch diameter, however any diameter hose 102 may be used without departing from the scope of the invention.

Figure 8:
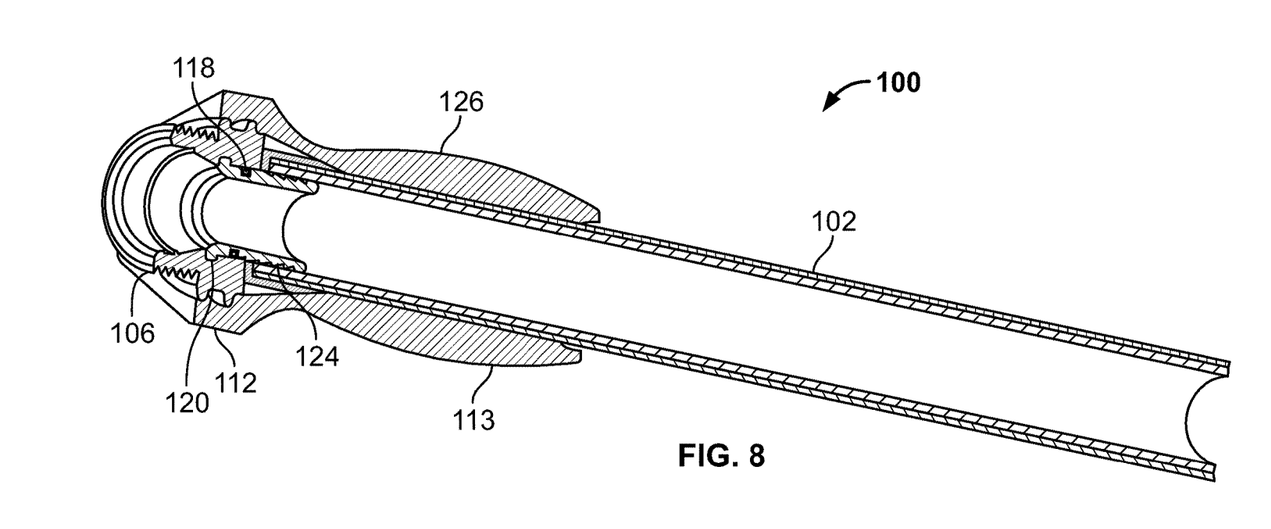
FIG. 8 is a cross-sectional side view of an embodiment of a freely rotating hose coupling device with an outer sleeve of the present invention.

Looking now to FIG. 8, it may be seen that the first larger diameter base 110 of the first coupling portion 104, the freely rotating connection 116, the O-ring 118, the second coupling portion 114, the coupling protrusion 122, and a portion of the hose 102 are all surrounded by the outer sleeve 112. Additionally, the ferrule 126 illustrated in FIG. 4 is also surrounded by the outer sleeve 112. Hence, the rigid structure of the outer sleeve 112 provides additional protection to the enclosed portion of the apparatus 100 as well as to the inner lining of the hose 102. The outer sleeve 112 essentially moves the bending point of the hose 102 further from the end of the hose 102. This especially protects the coupling protrusion 122 from damage due to external forces applied to the hose 102 such as bending or stepping on the hose 102. Additionally, this also protects the inner surface of the hose 102 and the hose 102 itself from damage due to puncture or other stresses from the rigid coupling protrusion 122 and barbs 124 in contact with the inner surface of the hose 102.

As described previously, the outer sleeve 112 of the preferred embodiment is connected to the first larger diameter base 110 of the first coupling portion 104. Thus, the outer sleeve 112 is able to move freely along a longitudinal axis with the first coupling portion 104 around the rest of the apparatus 100 and the surrounded portion of the hose 128.

Thus, the outer sleeve 112 and first coupling portion 104 may swivel independently of the rest of the apparatus 100 and hose 102. The preferred embodiment of the present invention contemplates a contoured outer sleeve 112 molded in a fashion to function as an ergonomic grip for a user. The outer sleeve 112 of the preferred embodiment includes an indented outer grip surface 113 which aids the user's hold on the apparatus 112 and hose 102. The outer grip surface 113 along with the ergonomic shape of the outer sleeve 112 in the preferred embodiment allows the user to maintain their grasp and control of the hose 102. However, it should be appreciated by one skilled in the art that the outer sleeve 112 and outer grip surface 113 can take on many forms and be made of many materials without departing from the scope of the invention.

As described previously, the outer sleeve 112 is able to swivel together with the first coupling portion 104 along a longitudinal axis around the remainder of the apparatus 100 as well as the hose 102. This enhances a user's ability to align and rotate the male end of the first coupling portion 104 onto a water hose accessory by giving the user a larger area to rotate as well as providing an ergonomic grip. The ergonomic grip is provided by the shape of the outer sleeve 112 and the outer indented surface 113 allowing the user to more easily rotate the male threaded end of the first coupling portion 104 with respect to the accessory to be mounted. Thus, installing and removing accessories, such as coupling the hose 102 to a pressure washer, is easier for a user of the present invention. In addition, the ability of the outer sleeve 112 and first coupling portion 104 to rotate freely around the remainder of the apparatus 100 and hose 102 allows for the easier coiling and uncoiling of a hose 102 and any attached accessory and also reduces thrashing of the hose 102 as it is moved from one location to another by the user.

Figure 9:
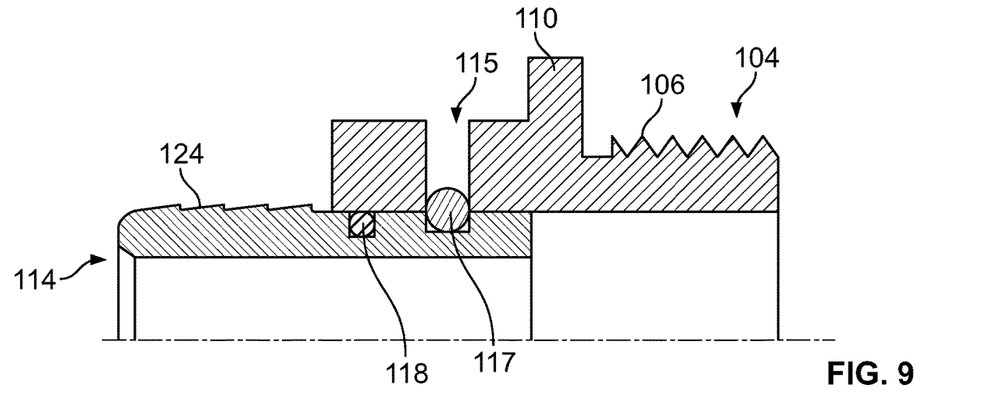
FIG. 9 is a cross-sectional schematic of an embodiment of a freely rotating hose coupling device of the present invention.
Figure 10:
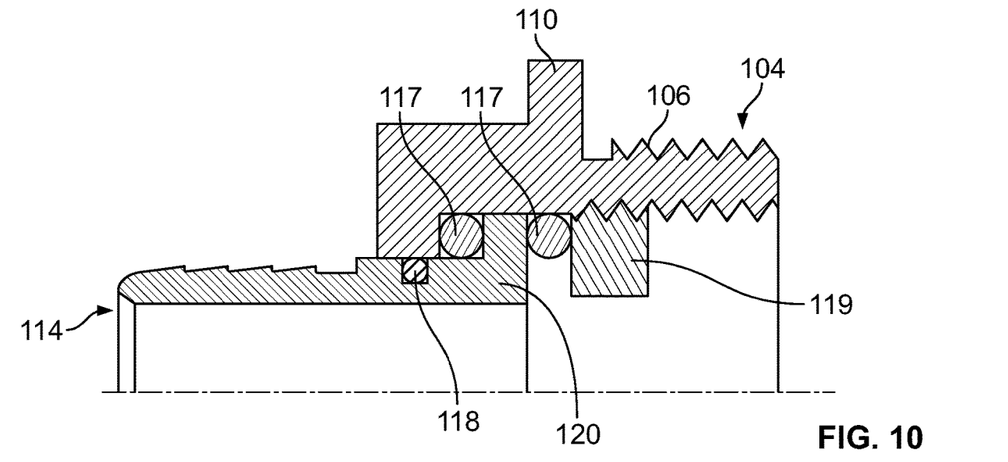
FIG. 10 is a cross-sectional schematic of an embodiment of a freely rotating hose coupling device of the present invention.
Figure 11:
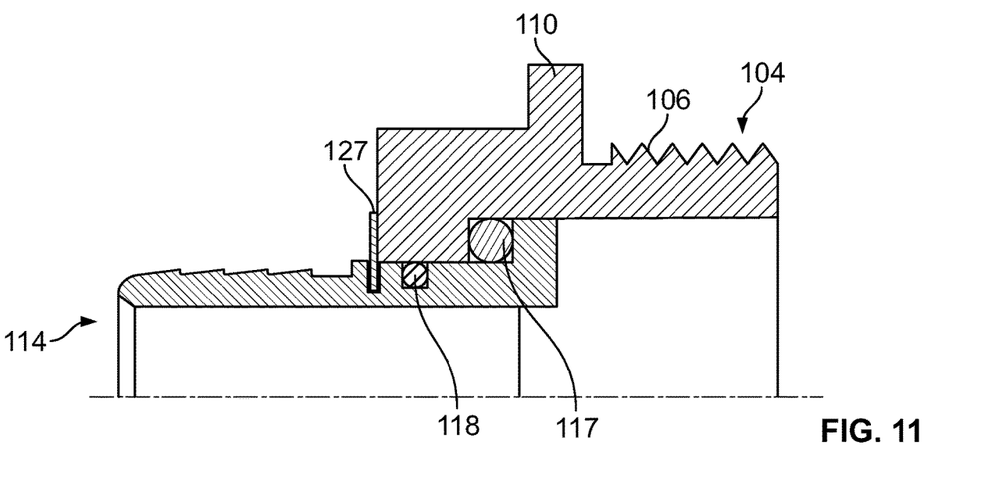
FIG. 11 is a cross-sectional schematic of an embodiment of a freely rotating hose coupling device of the present invention.

FIGS. 9, 10 and 11 depict contemplated alternative embodiments of the apparatus 100 in cross-sectional schematic views. FIG. 9 depicts the preferred embodiment of the present invention but includes an O-ring 118 behind the interior track and ball bearings 117 rather than in front at the first end 114a of the second coupling portion 114. FIG. 9 further depicts the second coupling portion 114 without a second larger diameter base 120, thus allowing the part to be machined from a smaller bar stock and utilizing less materials, thus saving costs. FIG. 10 illustrates an alternative embodiment utilizing friction-reducing/slick washers or similar ring type friction reducing agents 117. In the alternative embodiment one or more friction reducing/slick washers 117 are placed between the point of contact of the first and second coupling portions 104 and 114. Again, it should be appreciated by one skilled in the art, that any friction reducing component, such as ball bearings, may be used in conjunction with or as a substitute for the friction-reducing/slick washers 117 without departing from the scope of the present invention. Furthermore, in this embodiment the pin/plugging-nut 119 is placed within and surrounding the first inner opening 108 of the male threaded portion 106 of the first coupling protrusion 104. However, it should be appreciated by one skilled in the art that any form of locking mechanism that allows water to flow freely through it may be used without departing from the scope of the present invention. An additional friction-reducing/slick washer 117 is depicted behind the plug, but it should be appreciated by one skilled in the art that the friction-reducing/slick washers 117 can be placed in various locations to reduce the friction between the freely rotating connection 116 without departing from the scope of the present invention. Additionally, FIG. 11 depicts an alternative embodiment wherein the tapered coupling protrusion 122 of the preferred embodiment is substituted with a female coupling protrusion to allow a non-swivel hose to be adapted with the swivel hose coupling 100 of the present invention. Additionally, FIG. 11 depicts an alternative embodiment wherein the ball bearings 117 are integrated within the apparatus 100 during manufacture and, thus, do not require an access port 115 or pin 119 to lock the ball bearings within the apparatus 100. The first and second coupling portions 104 and 114 of the embodiment depicted in FIG. 11 are held together by one or more snap rings 127 within a complimentary groove. However, it should be appreciated by one skilled in the art that any connecting mechanism may be used with or without a corresponding groove without departing from the scope of the present invention.

Figure 12:
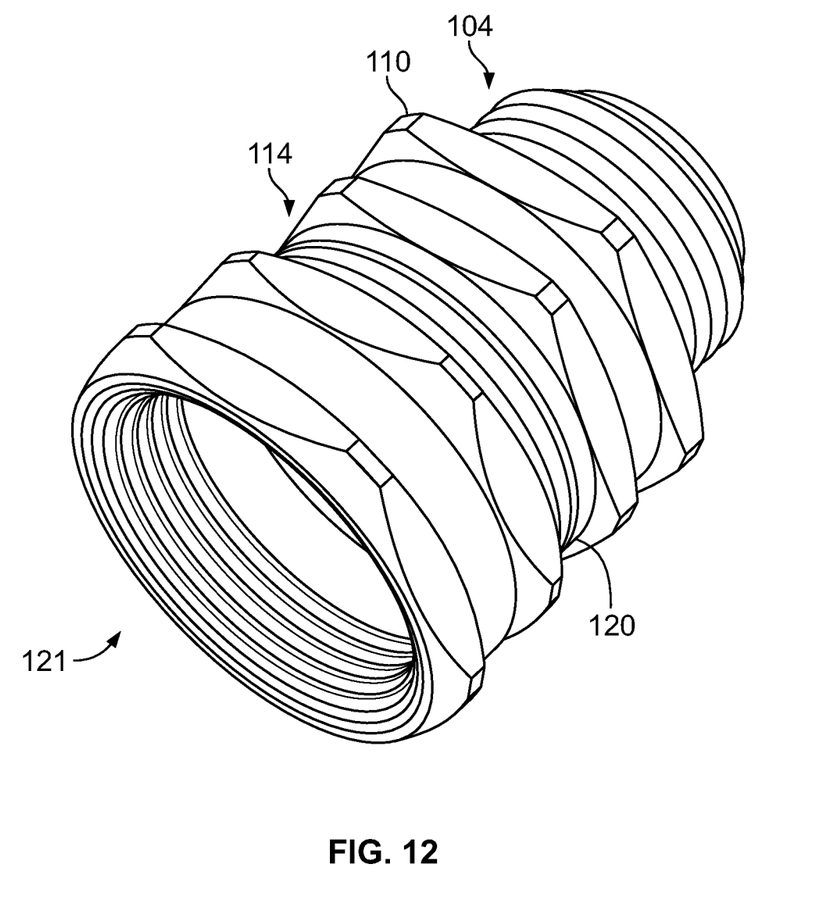
FIG. 12 is a perspective view of an embodiment of a freely rotating hose coupling device of the present invention.

Looking to FIG. 12, a perspective view of an alternative embodiment of the apparatus 100 is shown. In this alternative embodiment the first coupling portion 104 interfaces and connects with a second coupling portion 114 via the first coupling portion's 104 first larger diameter base 110. This creates a freely rotating connection 116 as discussed above. However, differentiated from the second coupling portion 114 of the preferred embodiment, the second coupling portion 114 does not taper to a barbed end 114b to accept a hose 102. Rather, in this alternative embodiment, the second larger diameter base 120 of the second coupling portion 114 is integral with a female coupling protrusion. The female coupling protrusion includes a third inner opening 121 to allow for the water from any connected hose 102 to freely flow through the device 100. Furthermore, the female coupling protrusion includes threads to accept the male end of a hose connector. It is further contemplated that the female coupling protrusion include a snap-ring/O-ring adapted on the innermost groove of the female coupling protrusion so as to aid in creating a seal with an interfaced male connector. The female coupling protrusion is contemplated to be of standard ¾ inch size as typically used for water hose couplings, however any diameter female coupling protrusion may be used without departing from the scope of the invention.

Figure 13:
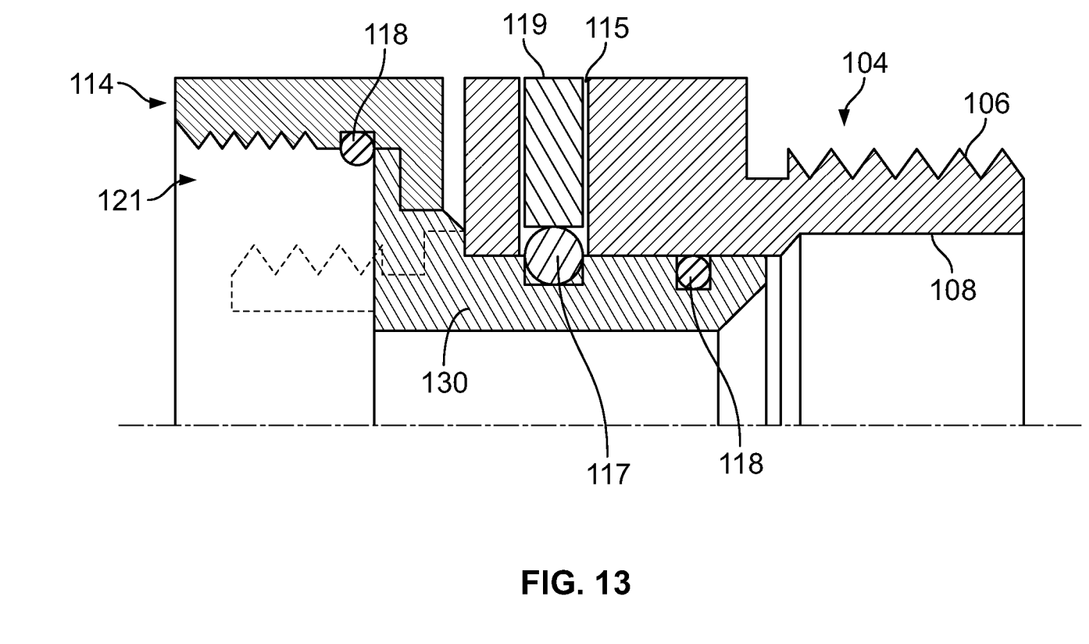
FIG. 13 is a cross-sectional schematic of an embodiment of a freely rotating hose coupling device of the present invention utilizing a third coupling portion in addition to a first and second coupling portion.

Looking now to FIG. 13, depicted is an alternative embodiment of the apparatus 100 utilizing a third/intermediary coupling portion 130 to create a freely rotating connection 116 between the first and second coupling portions 104 and 114. However, it should be appreciated by one skilled in the art that various numbers of intermediary parts can be used to connect the first and second coupling portions 104 and 114 to create a freely rotating connection 116 without departing from the scope of the invention. The alternative embodiment of FIG. 13 depicts the first coupling portion 104 interfacing and connecting with a third coupling portion 130. The third coupling portion 130 encapsulates the track of the first coupling portion 104 that holds the ball bearings 117 as discussed above. Additionally, the third coupling portion 130 includes an 118, however it should be appreciated by one skilled in the art that the O-ring 118 can have numerous placements or be removed without departing from the scope of the invention. The third coupling portion 130 also interfaces and connects with the second coupling portion 114. In this embodiment, the second coupling portion 114 consists of the female coupling protrusion or tapered coupling protrusion 122 to interface with a male threaded connector or hose 102, respectively.

Although various representative embodiments of this invention have been described above with a certain degree of particularity, those skilled in the art could make numerous alterations to the disclosed embodiments without departing from the spirit or scope of the inventive subject matter set forth in the specification and claims. Joinder references (e.g. attached, adhered, joined) are to be construed broadly and may include intermediate members between a connection of elements and relative movement between elements. As such, joinder references do not necessarily infer that two elements are directly connected and in fixed relation to each other. Moreover, network connection references are to be construed broadly and may include intermediate members or devices between a network connection of elements. As such, network connection references do not necessarily infer that two elements are in direct communication with each other. In some instances, in methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

Although the present invention has been described with reference to the embodiments outlined above, various alternatives, modifications, variations, improvements and/or substantial equivalents, whether known or that are or may be presently foreseen, may become apparent to those having at least ordinary skill in the art. Listing the steps of a method in a certain order does not constitute any limitation on the order of the steps of the method. Accordingly, the embodiments of the invention set forth above are intended to be illustrative, not limiting. Persons skilled in the art will recognize that changes may be made in form and detail without departing from the spirit and scope of the invention. Therefore, the invention is intended to embrace all known or earlier developed alternatives, modifications, variations, improvements, and/or substantial equivalents.

What is claimed is:
1. A hose coupling comprising;
 a. a first coupling portion;
 b. a second coupling portion;
 c. a freely rotating connection connecting said first and second coupling portions;
 d. wherein said second coupling portion further comprises a coupling projection connecting said hose coupling to at least one of a hose and a threaded male connector; and
 e. an outer coupling sleeve configured to rotate with said first coupling portion and extending fully over said freely rotating connection;
 g. wherein at least one of said first coupling portion and said second coupling portion further comprises an interior track;
 h. wherein said interior track receives and holds at least one friction reducing member; and
 i. wherein said at least one friction reducing member comprises at least one of at least one ball bearing and at least one friction-reducing washer.
2. A hose coupling comprising;
 a. a first coupling portion;
 b. a second coupling portion;
 c. a freely rotating connection connecting said first and second coupling portions;

d. wherein said second coupling portion further comprises a coupling projection connecting said hose coupling to at least one of a hose and a threaded male connector; and
e. an outer coupling sleeve configured to rotate with said first coupling portion and extending fully over said freely rotating connection;
g. wherein at least one of said first coupling portion and said second coupling portion further comprises an interior track;
h. wherein said interior track receives and holds at least one friction reducing member; and
i. wherein said interior track is accessible by an access port on said first coupling portion wherein a sealing member closes said access port to retain said at least one friction reducing member within said hose coupling.

3. The hose coupling of claim 2, wherein said interior track is fully encapsulated by interfacing said second coupling portion with said first coupling portion wherein said fully encapsulated track, holding said at least one friction reducing member, allows said first coupling portion to freely rotate in relation to said second coupling portion along their longitudinal axis.

* * * * *